United States Patent
Mulligan et al.

(10) Patent No.: US 6,865,419 B2
(45) Date of Patent: Mar. 8, 2005

(54) METHOD AND APPARATUS FOR MEASUREMENT OF MEAN PULMONARY ARTERY PRESSURE FROM A VENTRICLE IN AN AMBULATORY MONITOR

(75) Inventors: Lawrence J. Mulligan, Andover, MN (US); Tom D. Bennett, Shoreview, MN (US)

(73) Assignee: Medtronic, Inc., Minneapolis, MN (US)

(*) Notice: Subject to any disclaimer, the term of this patent is extended or adjusted under 35 U.S.C. 154(b) by 365 days.

(21) Appl. No.: 09/997,753

(22) Filed: Nov. 30, 2001

(65) Prior Publication Data

US 2002/0103442 A1 Aug. 1, 2002

Related U.S. Application Data

(60) Provisional application No. 60/250,420, filed on Dec. 1, 2000.

(51) Int. Cl.[7] .................. A61B 5/0402; A61N 1/365
(52) U.S. Cl. .................. 607/23; 600/513; 600/486
(58) Field of Search ............... 600/483–488, 600/513, 521, 522; 607/17, 23

(56) References Cited

U.S. PATENT DOCUMENTS

| | | | |
|---|---|---|---|
| 4,310,000 A | 1/1982 | Lindemans | |
| 4,407,288 A | 10/1983 | Langer et al. | |
| 4,428,378 A | 1/1984 | Anderson et al. | |
| 4,532,931 A | 8/1985 | Mills | 128/419 PG |
| 4,667,680 A | * 5/1987 | Ellis | 600/485 |
| 4,821,723 A | 4/1989 | Baker, Jr. et al. | |
| 4,865,036 A | 9/1989 | Chirife | |
| 4,967,747 A | 11/1990 | Carroll et al. | |
| 4,984,572 A | * 1/1991 | Cohen | 607/6 |
| 5,158,078 A | 10/1992 | Bennett et al. | |
| 5,176,137 A | 1/1993 | Erickson et al. | |
| 5,195,535 A | 3/1993 | Shank | |
| 5,209,229 A | 5/1993 | Gilli | |
| 5,226,413 A | 7/1993 | Bennett et al. | |
| 5,312,453 A | 5/1994 | Shelton et al. | |
| 5,314,430 A | 5/1994 | Bardy | |
| 5,318,593 A | 6/1994 | Duggan | |
| 5,330,505 A | 7/1994 | Cohen | |
| 5,331,966 A | 7/1994 | Bennett et al. | |
| 5,353,752 A | 10/1994 | Suzuki | |
| 5,353,800 A | 10/1994 | Pohndorf et al. | |
| 5,368,040 A | 11/1994 | Carney | |
| 5,535,752 A | 7/1996 | Halperin et al. | |
| 5,544,661 A | * 8/1996 | Davis et al. | 600/513 |
| 5,564,434 A | 10/1996 | Halperin et al. | |
| 5,662,688 A | 9/1997 | Haefner et al. | |
| 5,810,735 A | 9/1998 | Halperin et al. | |
| 5,855,893 A | 1/1999 | Weinkauf et al. | |
| 5,902,324 A | 5/1999 | Thompson et al. | |
| 6,070,100 A | 5/2000 | Bakels et al. | |
| 6,070,101 A | 5/2000 | Struble et al. | |
| 6,113,548 A | 9/2000 | DeBoisblanc et al. | 600/485 |
| 6,223,079 B1 | 4/2001 | Bakels et al. | |

* cited by examiner

Primary Examiner—Jeffrey R. Jastrzab
(74) Attorney, Agent, or Firm—Girma Wolde-Michael; Daniel G. Chapik

(57) ABSTRACT

A system and method for determining mean pulmonary arterial pressure (MPAP) using a pressure sensor located within a ventricle of a heart, and a signal indicative of cardiac electrical activity such as an electrocardiogram (EGM) signal. The pressure may be sensed within the right and/or left ventricle using an implanted pressure sensor. The sensed pressure may be used to determine the Ventricular Systolic Pressure (VSP) and an estimated Pulmonary Arterial Diastolic pressure (ePAD). The VSP, ePAD, and time intervals associated with systole and diastole may then be used to obtain an MPAP that closely approximates mean pulmonary arterial pressure measured using a sensor located in the pulmonary artery.

23 Claims, 6 Drawing Sheets

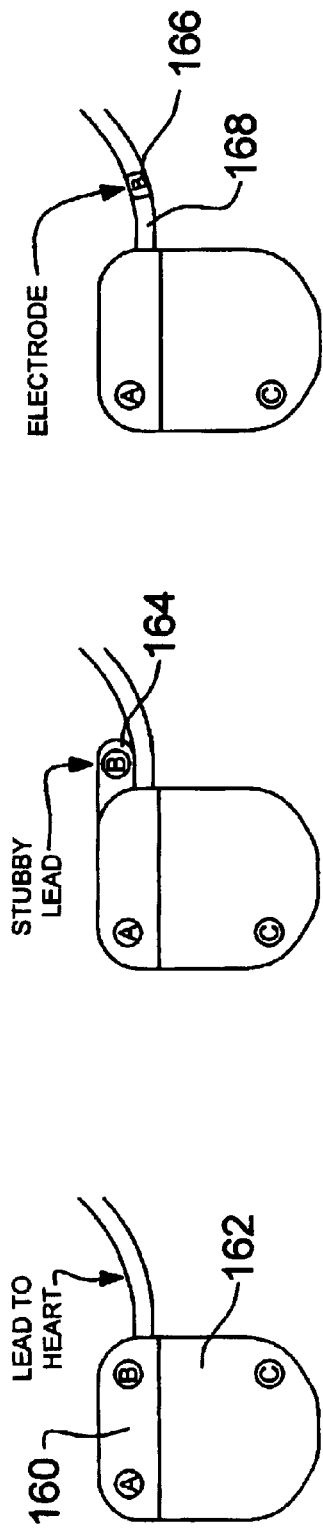
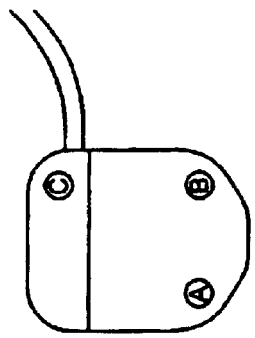
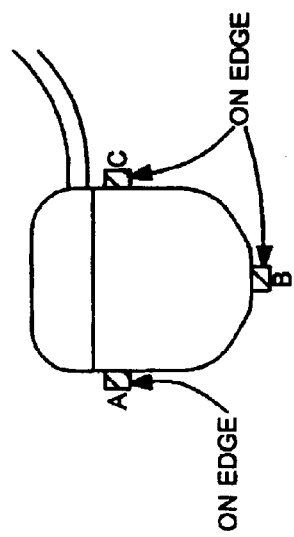

METHOD AND APPARATUS FOR MEASUREMENT OF MEAN PULMONARY ARTERY PRESSURE FROM A VENTRICLE IN AN AMBULATORY MONITOR

RELATED APPLICATIONS

This application claims priority to provisionally-filed application Ser. No. 60/250,420 filed Dec. 1, 2000, which is incorporated herein by reference in its entirety.

FIELD OF THE INVENTION

This invention relates to measuring arterial pressure; and more specifically, relates to system and method for measuring mean arterial pressure using an ambulatory monitor.

DESCRIPTION OF THE PRIOR ART

Mean Pulmonary Artery Pressure (MPAP) is an important indicator of cardiovascular health. For example, the management of some diseases depends upon an accurate indication of pulmonary vascular resistance, which is determined using mean Pulmonary Arterial (PA) pressure. MPAP is also used as a general indicator of the work load of the right ventricle, and can therefore be used to diagnose and monitor heart failure.

In the past, mean PA pressure has been determined using several methods, all of which require a pressure sensor that is located within the pulmonary artery. According to a first method, both the PA systolic and PA diastolic pressure measurement values are used to determined MPAP using the following equation:

$$MPAP = \tfrac{1}{3}(\text{Systolic Pressure}) + \tfrac{2}{3}(\text{Diastolic Pressure})$$

This equation is based on the premise that in an average cardiac cycle, one-third of the time is spent in systole, and the remaining two-thirds of the time is spent in diastole. This is generally only true, however, when a patient is at rest. To provide a more accurate estimation of MPAP during a period of exercise, the above-described equation may be altered to reflect the fact that when a heart rate is above 100 or 120 beats-per-minute, the ventricles are in systole during approximately half of the cardiac cycle, and in diastole the other half of the cycle. This method does not, however, provide an accurate overall MPAP measurement that reflects both periods of rest and exercise.

Another method of measuring MPAP involves filtering the pressure signal as generated by the pressure sensor to remove signal pulsatility. This may be accomplished using a digital filter, for example. The resulting signal value is a close approximation of the MPAP. Although this is more accurate than using diastolic and systolic pressures to calculate MPAP, the filtering process requires a relatively long time constant. Therefore, beat-to-beat measurements cannot be obtained.

According to yet another method, the pressure signal is integrated over a cardiac cycle, and then the resulting sum is divided by a number of predetermined time increments that were included in the cycle. This provides an accurate beat-by-beat average pressure. This method has the disadvantage, however, of requiring a digital signal processing system that is not readily available in most clinical settings.

What is needed, therefore, is an improved system and method for determined MPAP, which provides accurate beat-to-beat average measurements, and can be readily ascertained in a clinical setting. Preferably, such a device does not require the use of a pressure sensor located within the pulmonary artery.

SUMMARY OF THE INVENTION

The current invention provides a system and method for determining MPAP without the use of a sensor located within the pulmonary artery. The MPAP value is derived using a pressure measurement obtained from within a heart chamber, and a second signal indicative of cardiac electrical activity such as an electrocardiogram (EGM) signal.

According to the current invention, pressure may be sensed within the right and/or left ventricle using one or more implanted pressure sensors. The sensed pressure may be used to determine the Ventricular Systolic Pressure (VSP), which is the maximum pressure measured at any time throughout the cardiac cycle. This sensed pressure may further be used to derive an estimated Pulmonary Arterial Diastolic pressure (ePAD), which is the pressure at the time the change in pressure over time is at a maximum. Finally, the EGM and pressure signals may be used to determine the time the heart spends both in systole and diastole. By multiplying the VSP by the time spent in systole, further multiplying the ePAD by the time spent in diastole, then adding the two values, mean pulmonary arterial pressure is closely approximated.

According to one embodiment of the invention, the system is included within an implantable medical device (IMD) such as a pacemaker, cardioverter/defibrillator, drug delivery device, or another type of device for delivering therapy to a patient. The derived MPAP value may be utilized to control therapy delivery. According to one aspect of the invention, the IMD provides cardiac resynchronization therapy, which may be monitored and controlled using the MPAP value. In another embodiment, the derived MPAP value may be used to control the delivery of a biologically-active agent to the patient.

Processing steps performed according to the current invention are carried out by a processing circuit which may be implanted within the body, or which is located external to the patient. In one embodiment, the processing circuit includes first and second portions, wherein the first portion is located within an implantable device, wherein the second portion is located within a device external to the patient such as a programmer, and wherein the system further includes a communication circuit to transfer data signals between the first and second portions. For example, the pressure and EGM signals may be transferred via a communication circuit to an external device so that all, or some, of the processing is completed by the external device.

According to one embodiment, the invention includes a system for estimating mean pulmonary arterial pressure of a patient. The system comprises a sensor located in a ventricle of a heart to measure pressure, a circuit to measure electrocardiogram (EGM) signals, and a processing circuit to derive mean pulmonary arterial pressure (MPAP) from the pressure and the EGM signals. According to another embodiment of the invention, a method is provided for determining mean pulmonary arterial pressure (MPAP). The method includes sensing pressure within a ventricle of a heart, sensing an electrocardiogram (EGM) signal of the heart, and using the sensed pressure and the EGM signal to derive the MPAP.

Other scopes and aspects of the invention will become apparent to those skilled in the art from the drawings and the accompanying description.

BRIEF DESCRIPTION OF THE DRAWINGS

FIG. 3A is a side view of a pulse generator illustrating a subcutaneous electrode array as may be used with the current invention.

FIG. 3B is a side view of a pulse generator having an electrode array wherein at least one of the electrodes extends away from the pulse generator by a lead extension member.

FIG. 3C is a side view of a pulse generator wherein at least one of the electrodes or an electrode array is located at a proximal end of a lead.

FIG. 3D is a side view of a pulse generator wherein multiple electrodes of an electrode array are located on an edge of a device housing.

FIG. 3E is a side view of yet another embodiment of a device housing including an array of electrodes.

DETAIL DESCRIPTION OF THE DRAWINGS

The current invention provides a system and method for determining mean pulmonary arterial pressure (MPAP) using a pressure measurement obtained from within a heart chamber in conjunction with a second signal indicative of cardiac electrical activity such as an electrocardiogram (EGM) signal. Thus, the current invention eliminates the need for a pressure sensor located in the pulmonary artery.

Figure 1:
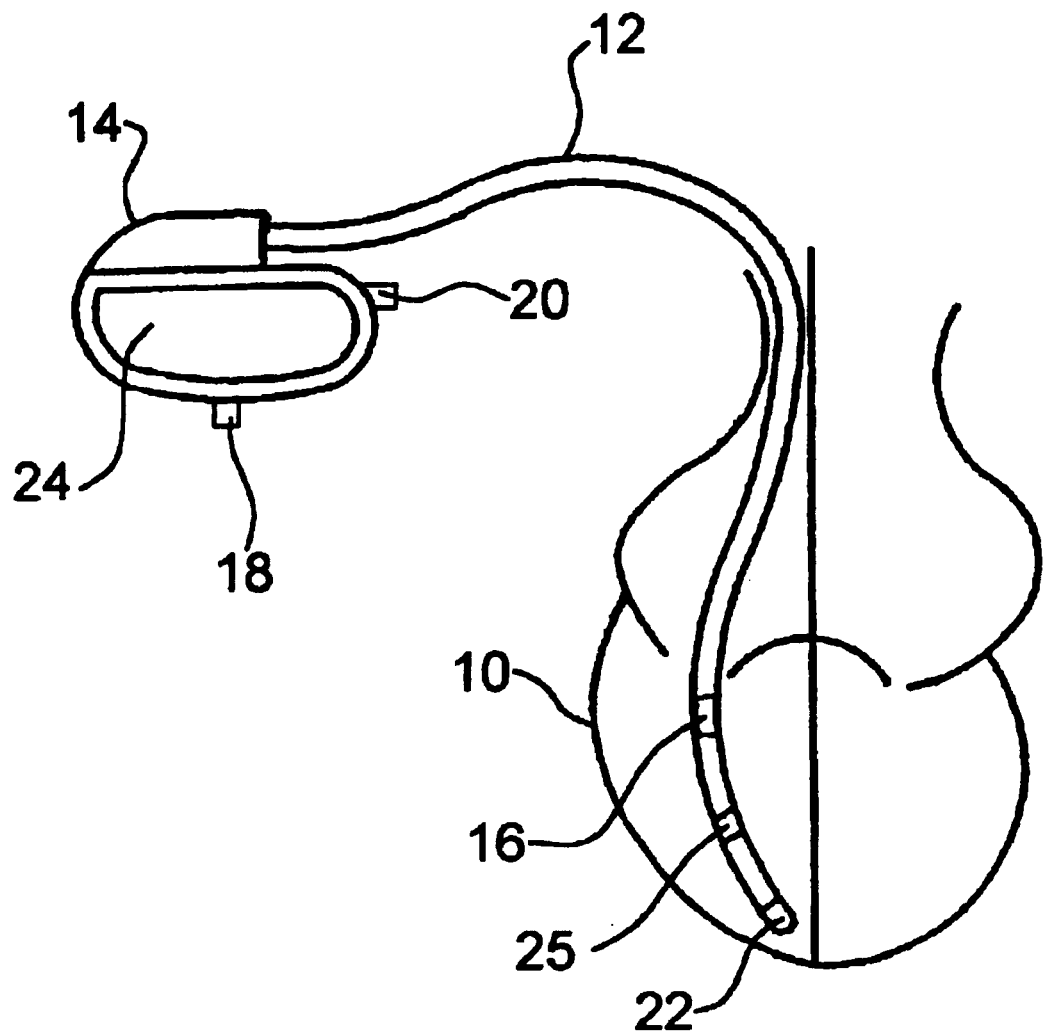
FIG. 1 is a schematic representation of an implanted medical device (IMD) as may be used with the current invention.

FIG. 1 is a schematic representation of an implanted medical device (IMD) 14 as may be used with the current invention. This EMD may be any device that is capable of measuring pressure signals from within a ventricle of a patient's heart, and which may further be capable of measuring the patient's electrocardiogram (EGM). Such a device may be a hemodynamic monitor such as the Chronicle ™ device commercially available from the Medtronic Corporation. Circuitry included in the Chronicle is described in commonly-assigned U.S. Pat. Nos. 5,535,752 and 5,564,434 which are incorporated herein by reference in their entireties. Alternatively, the device may be a pacemaker, or a cardioverter/defibrillator. Exemplary pacemaker systems that may be used to practice the current invention are described in commonly-assigned U.S. Pat. Nos. 5,158,078, 5,318,593, 5,312,453, and 5,226,413, which are incorporated herein by reference in their entireties. Any other pacing system known in the art may be adapted for use in the alternative. The IMD may additionally, or in the alternative, include cardioversion/defibrillation circuitry as described in commonly-assigned U.S. Pat. Nos. 5,193,535, and 5,314,430, which are incorporated herein by reference in their entireties. Other devices such as implantable drug delivery devices may also be adapted for use with the current invention.

Returning to FIG. 1, the IMD 14 may be implanted subcutaneously, between the skin and the ribs. Other implantation sites may be used if appropriate. In one embodiment, a lead 12 is passed through a vein into the right ventricle of the heart 10. The distal end of the lead or catheter may have a tip electrode 22 contacting the interior of the heart. In a multipolar configuration, a second ring electrode 25 may be spaced from the tip electrode 22. Each of these electrodes is connected to the circuitry contained in the IMD 14. Alternatively, a unipolar mode made be used wherein a portion of the metallic enclosure or "can" of the IMD may form an electrode surface 24. The EGM signal is measured between this surface and an implanted electrode such as the tip electrode 22. In yet another embodiment, a Subcutaneous Electrode Array (SEA) such as electrodes 18 and 20 may be located on, but electrically isolated from, the housing of the implantable device such as disclosed in U.S. Pat. No. 5,331,966, incorporated herein by reference in its entirety.

Additional leads (not shown) may be coupled to IMD, including a lead located within the right atrium, and/or a lead located within a coronary vessel such as the coronary sinus. These leads may further include one or more high-voltage electrodes for providing cardioversion/defibrillation therapy.

Lead 12 is shown to further include a pressure sensor 16. If desired, an additional lead coupled to IMD 14 may be provided to carry the pressure sensor. The pressure sensor is preferably located within the right ventricle, although it may also be located within the left ventricle in a manner to be discussed below. Pressure sensors and accompanying circuitry as may be adapted for use with the current invention are described in commonly-assigned U.S. Pat. Nos. 5,353,752, 5,353,800, 5,564,434, 5,330,505, and 5,368,040 which are incorporated herein by reference in their entireties.

Figure 2:
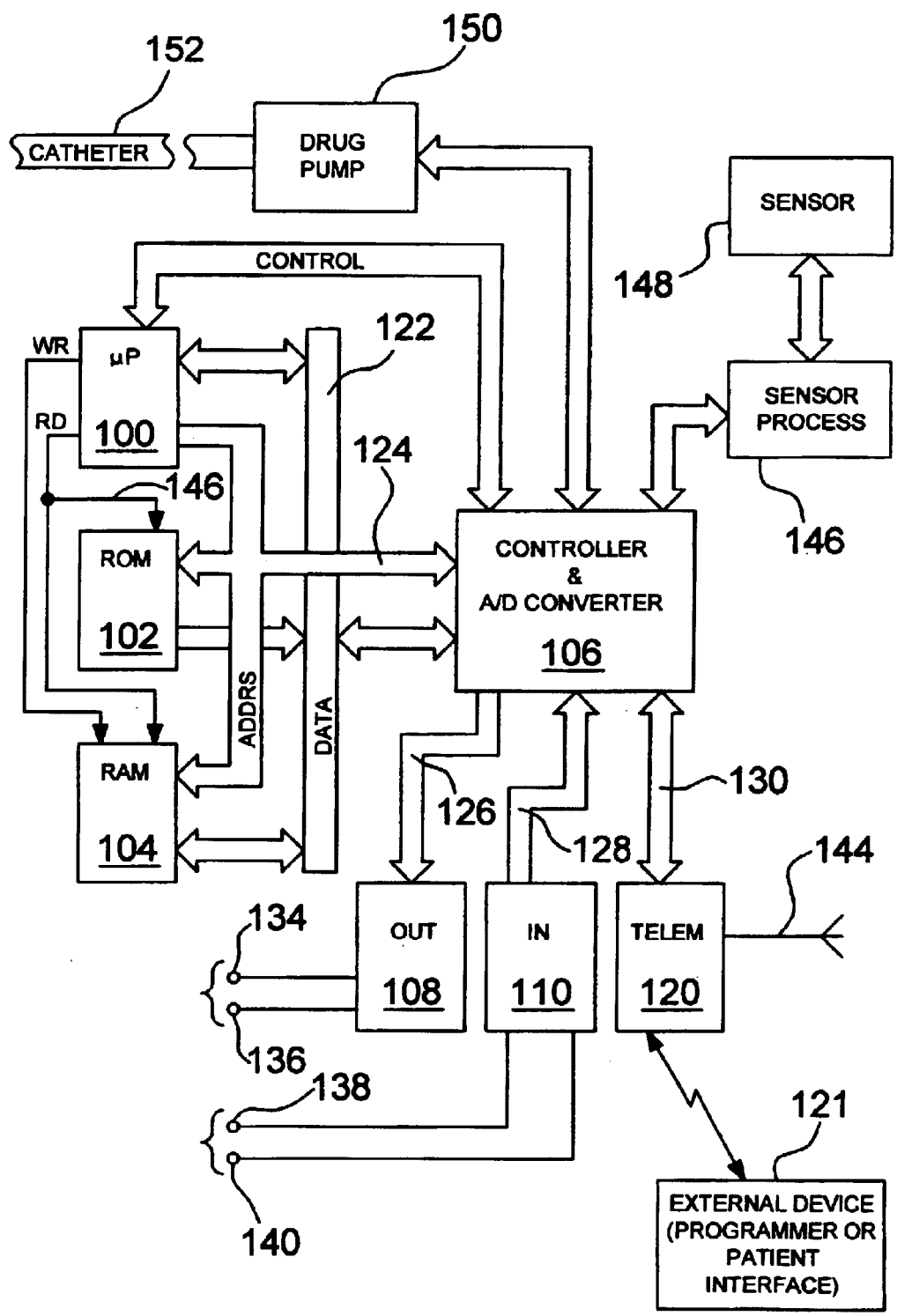
FIG. 2 is a block functional diagram of an illustrative embodiment of a pulse generator that may be employed according to the present invention.

FIG. 2 is a block functional diagram of an illustrative embodiment of a pulse generator that may be employed according to the present invention. It may be noted that pulse generation capabilities are not necessary for practicing the current invention, and the following discussion is therefore to be considered exemplary only.

The primary elements of the exemplary apparatus illustrated in FIG. 2 include a microprocessor 100, read-only memory (ROM) 102, random-access memory (RAM) 104, a digital controller 106, an input amplifier circuit 110, an output circuit 108, and a telemetry/programming unit 120.

Within the current embodiment, data processing capabilities and device control functions are provided by microprocessor 100. It will be understood that other digital and/or analog circuitry embodiments are within the scope of the invention. For example, the configurations illustrated in U.S. Pat. No. 5,251,624 issued to Bocek et al., U.S. Pat. No. 5,209,229 issued to Gilli, U.S. Pat. No. 4,407,288, issued to Langer et al, U.S. Pat. No. 5,662,688, issued to Haefner et al., U.S. Pat. No. 5,855,893, issued to Olson et al., U.S. Pat. No. 4,821,723, issued to Baker et al., and/or U.S. Pat. No. 4,967,747, issued to Carroll et al., all incorporated herein by reference in their entireties, may be usefully employed in conjunction with the present invention. Alternatively, or additionally, processing capabilities may be provided by an external processing circuit in a manner to be discussed below.

Read-only memory stores software and/or firmware for the IMD, including the primary instruction set executed by microprocessor 100. These instructions define the methods performed by the microprocessor according to the current invention. These instructions may also control any therapy and/or monitoring functions performed by the device. Additional storage is provided by RAM 104, which generally stores variable control parameters, such as programmed pacing parameters. Random-access memory 104 may also store digitized signals indicative of EGM waveforms and pressure measurements, as well as values that are derived from these measured signals during calculation of the MPAP.

Controller 106 performs basic control and timing functions of the device. Controller 106 may include at least one programmable timing counter, which is used to measure timing intervals such as R—R intervals used in the current invention. The timer counter may also control delivery of stimulation pulses in a manner known in the art. Analog-to-digital conversion (A/D) logic may be provided by the controller or a separate circuit to transform analog EGM and pressure signals to digitized samples that may be stored in memory such as RAM 104 and processed as described below.

In one embodiment, controller 106 may be utilized to generate corresponding interrupts on control lines 132 to microprocessor 100, allowing the microprocessor to perform any required mathematical calculations, including all operations associated with processing of the MPAP indicator. Alternatively, controller may directly transfer measured signal values to an external device for processing in a manner to be discussed below.

Optional output stage 108 may provide the ability to deliver stimulation pulses to tissue. For example, output stage 108 is shown coupled to terminals 134 and 136, which may, in turn, be electrically coupled to respective electrodes such as tip electrode 22 and ring electrode 25 (FIG. 1). Alternatively, or in addition, high-voltage electrodes may be coupled to output stage 108 as is known in the art to provide cardioversion/defibrillation shocks to a patient. Additional electrodes may be so coupled to provide stimulation therapy to nerve or other tissue as needed. In sum, output stage may be adapted to provide any type of stimulation known in the art.

In one embodiment, output stage 108 includes means for pacing on both sides of the heart. This type of therapy may be provided to resynchronize the heart and optimize cardiac output. Such therapy is described in commonly-assigned U.S. Pat. Nos. 6,223,079, 6,070,100, 6,070,101, and 5,902,324 incorporated herein by reference, although any type of resynchronization therapy known in the art may be used in conjunction with the current invention.

In cardiac resynchronization therapy, pacing on the right side of the heart is generally accomplished by locating one or more leads in the right atrium or ventricle, as set forth above. Similarly, pacing of the left side of the heart may be accomplished using one or more leads positioned within, or adjacent to, the left atrium or ventricle. Often, pacing on the left side of the heart is accomplished by positioning at least one lead within the coronary sinus in proximity to the left side of the heart. The timing associated with the various pacing pulses delivered on the left and right sides of the heart may then be adjusted based on pressure estimates obtained according to the current invention. For example, the V—V timing interval associated with pulses delivered in the right and left ventricles may be adjusted based on MPAP estimates. This is discussed further below.

Turning now to a discussion of the input circuit 110, this circuit is used to sense signals such as the EGM signals. This circuit is shown coupled to terminals 138 and 140, which, in turn, may be respectively coupled to electrodes such as tip electrode 22 and ring electrode 25 to sense EGM signals. Alternatively, if a unipolar mode of sensing is employed, signals may be sensed between one of the implanted electrodes and the device housing or an electrode on the device housing. Sensing may also be performed subcutaneously or externally, as discussed further below.

Input circuit 110 may include amplification, and noise detection and protection circuitry. Signal sensing may be disabled during periods of excessive noise, if desired. Noise rejection filters and similar circuitry may also be included, as is known in the art. In one embodiment, input circuit 110 may provide signals indicating both the occurrence of natural ventricular beats and paced ventricular beats to the controller 106 via signal lines 128. In one embodiment, controller 106 provides digitized signals indicative of the occurrence of such ventricular beats to microprocessor 100 via signal lines 132, which may be in the form of interrupts. This allows the microprocessor to perform any necessary calculations or to update values stored in RAM 104 according to the current invention.

As discussed above, the device also includes a pressure sensor 148 to sense pressure within the cardiac system. Pressure may be sensed within the right ventricle using a sensor such as sensor 16 positioned on a lead coupled to the IMD (FIG. 1). Alternatively, a sensor placed within the left ventricle may be used in a manner discussed below. The pressure sensor 148 may include one or more of the pressure sensing circuits known in the art, including those discussed above.

It may be noted that other sensors may also be coupled to the IMD of FIG. 2, including a hemodynamic sensor such as an impedance sensor disclosed in U.S. Pat. No. 4,865,036 issued to Chirife. Alternatively, a demand sensor may be included for measuring cardiac output parameters, such as an oxygen saturation sensor disclosed in U.S. Pat. No. 5,176,137, issued to Erickson et al. or a physical activity sensor as disclosed in U.S. Pat. No. 4,428,378, issued to Anderson et al., both of which are incorporated herein by reference in their entireties. Any other types of physiological sensors known in the art may be included in the system to develop patient data that may be used in conjunction with the MPAP to diagnose patient conditions and aid in adjusting therapy.

Sensor processing circuitry 146 controls pressure sensor 148 and any other physiological sensors, and provides the signals to the controller 106 so that the signals may be transformed into digital representations. Sensor signals may also be stored in RAM 104 for later diagnostic use.

External control of the IMD is accomplished via a communication circuit such as telemetry/control block 120. Any conventional programming/telemetry circuitry is believed workable in the context of the present invention. Information may be provided to the IMD 10 from an external device 121 and passed to controller 106 via control lines 130. Similarly, information from the IMD may be provided to the telemetry block 120 via control lines 130 and thereafter transferred to the external device. This information may include signal data such as EGM signals and pressure measurements, or may include any of the derived intermediate values discussed below. Some, or all, of the processing associated with derivation of the MPAP indicator may then be performed outside of the IMD by a processing circuit included within external device 121 or within another data processing system. Transfer of data from the external device to another data processing system may be accomplished via a wireless communication link, for example. If desired, pressure measurements, the EGM signals, and/or any derived data such as intermediate values and the MPAP indicator may be transferred to a patient file within a centrally-located database for use in monitoring and diagnosing patient conditions.

In one embodiment, the external device 121 is a programmer that may be utilized to diagnose patient conditions and to provide any necessary re-programming functions. In another embodiment, the external device may be a patient interface used to provide information to, and/or receive commands from, the patient. For example, the patient interface may be an externally-worn device such as a wrist band. In one embodiment, a warning may be provided to the patient interface when the MPAP is outside of a predetermined range. This may alert the patient to seek medical attention.

In yet another embodiment of the invention, the implantable device includes a drug pump 150 as shown in FIG. 2. This pump may be used to deliver a biologically-active agent to the patient. Such drug delivery may be adjusted based on the MPAP value, as will be discussed further below.

As noted above, the EGM signals may be obtained using one or more leads positioned within heart chambers. Alternatively, one or more electrodes positioned on the housing of an IMD may also be used for this purpose as described in commonly-assigned U.S. Pat. No. 5,331,966, which is incorporated herein by reference in its entirety. This type of array, which is provided by the Medtronic Model 9526 Reveal Plus Implantable Loop Recorder, includes at least two sensing electrodes on the can for sensing of cardiac signals. In all such systems, it will be understood that the electrodes A, B, C on the surface of the housing are electrically isolated from one another and the conductive surface of the IMD housing through suitable insulating bands and electrical feedthroughs as described in U.S. Pat. No. 4,310,000, incorporated herein by reference. Examples of possible electrode orientations and configurations of a three electrode system comprising the electrodes are set forth in FIGS. 3A through 3E.

FIG. 3A is a side view of an IMD illustrating the orientation of orthogonally-disposed electrodes A, B and C with two electrodes on the connector block 160 and one electrode on the pulse generator case 162. The spacing of the electrodes A, B and C on each of the illustrated orientations of FIG. 3A through 3E may be on the order of about one inch but can be larger or smaller depending on the exact size of the device. Smaller devices and closer spacing will require greater amplification.

FIG. 3B is a side view of an IMD wherein at least one of the electrodes extends away from the pulse generator by a lead extension member 164 to achieve a greater inter-electrode spacing, if desirable.

FIG. 3C is a side view of an IMD wherein at least one of the electrodes 166 is located at a proximal end of a lead 168.

FIG. 3D is a side view wherein multiple electrodes are located on an edge of a device housing. It will be understood that the electrodes placed on the edge of the pulse generator case could constitute insulated pins of feedthroughs extending through the wall of the case. As illustrated in FIGS. 3C and 3D, the relative orientation of the electrodes may vary somewhat from the orthogonal orientation depicted in FIGS. 3A and 3B.

FIG. 3E is a side view of yet another embodiment of a device housing including an array of electrodes.

In yet another embodiment, cardiac potential signals are obtained using one or more electrodes located externally on the patient's body to measure an ECG signal. These signals may be correlated with the measured pressure signals using timestamps. Such correlated measurements could be processed by an external processing circuit as discussed above according to the current inventive method. Alternatively, these signals could be transferred to the IMD via a communication system such as telemetry circuit 120. Thereafter, the MPAP may be generated by a processing circuit within the IMD.

Discussion may now turn to the method used to derive the MPAP. At least two measurements are required including an intercardiac pressure signal measured within the right or left ventricle, and an EGM signal. These values are used to derive the following values:

1.) The Ventricular Systolic Pressure (VSP), which is the maximum pressure that is measured at any time throughout the cardiac cycle, is determined from the sensed ventricular pressure. It may be noted that although this pressure may be measured within a ventricle, and is preferably measured within the right ventricle, this measurement closely approximates the pulmonary arterial systolic pressure unless stenosis of the pulmonic valve is present.

2.) The estimated Pulmonary Artery Diastolic pressure (ePAD), which is a measure of the ventricular pressure at the time the change in the pressure signal over time (dp/dt) is at a maximum, is determined from the sensed ventricular pressure. As is similar to the case of the VSP measurement, this ventricular measurement closely approximates the pulmonary arterial diastolic pressure unless stenosis of the pulmonic valve is present.

3.) The time between successive R waves in the cardiac cycle (R—R interval) may be determined using the EGM signal. In one embodiment wherein the invention is incorporated into a pacing device, this could include a time between paced and/or sensed beats.

4.) The Systolic Time Interval (STI), which is the time the heart is spent in systole, may be estimated by measuring the time from the start of an R wave to the time when the change in pressure over time (dp/dt) is at a maximum. This determination therefore involves use of both the EGM and the pressure signal.

The foregoing measurements and derived values may be used to determine the fractional portion of the time spent in both systole and diastole, as follows:

The Diastolic Time Interval (DTI) may be obtained by subtracting the STI from the R—R interval:

$$DTI = R\text{—}R \text{ Interval} - STI.$$

The fractional portion of the time the heart is in diastole may then be calculated as follows:

$$DTI/(R\text{—}R \text{ Interval}).$$

Similarly, the fractional portion of the time spent in systole may also be calculated as follows:

$$STI/(R\text{—}R \text{ Interval}).$$

Finally, these fractional values may be used to determine a more accurate value for MPAP as follows:

$$MPAP = [(DTI/R\text{—}R \text{ Interval}) \times ePAD] + [(STI/R\text{—}R \text{ Interval}) \times VSP].$$

Simply put, the estimated diastolic pressure ePAD is multiplied by the time spent in diastole, the estimated systolic pressure VSP is multiplied by the time spent in systole, and the two products are added together to create an average Mean Pulmonary Arterial Pressure measurement. This determination is more accurate than an estimate that merely uses a predetermined fractional value to represent time spent in systole and diastole. Moreover, the current invention does not require use of a pressure sensor located within the pulmonary artery. Additionally, the invention provides a measurement that is available on a beat-to-beat basis using the current invention.

Figure 4:
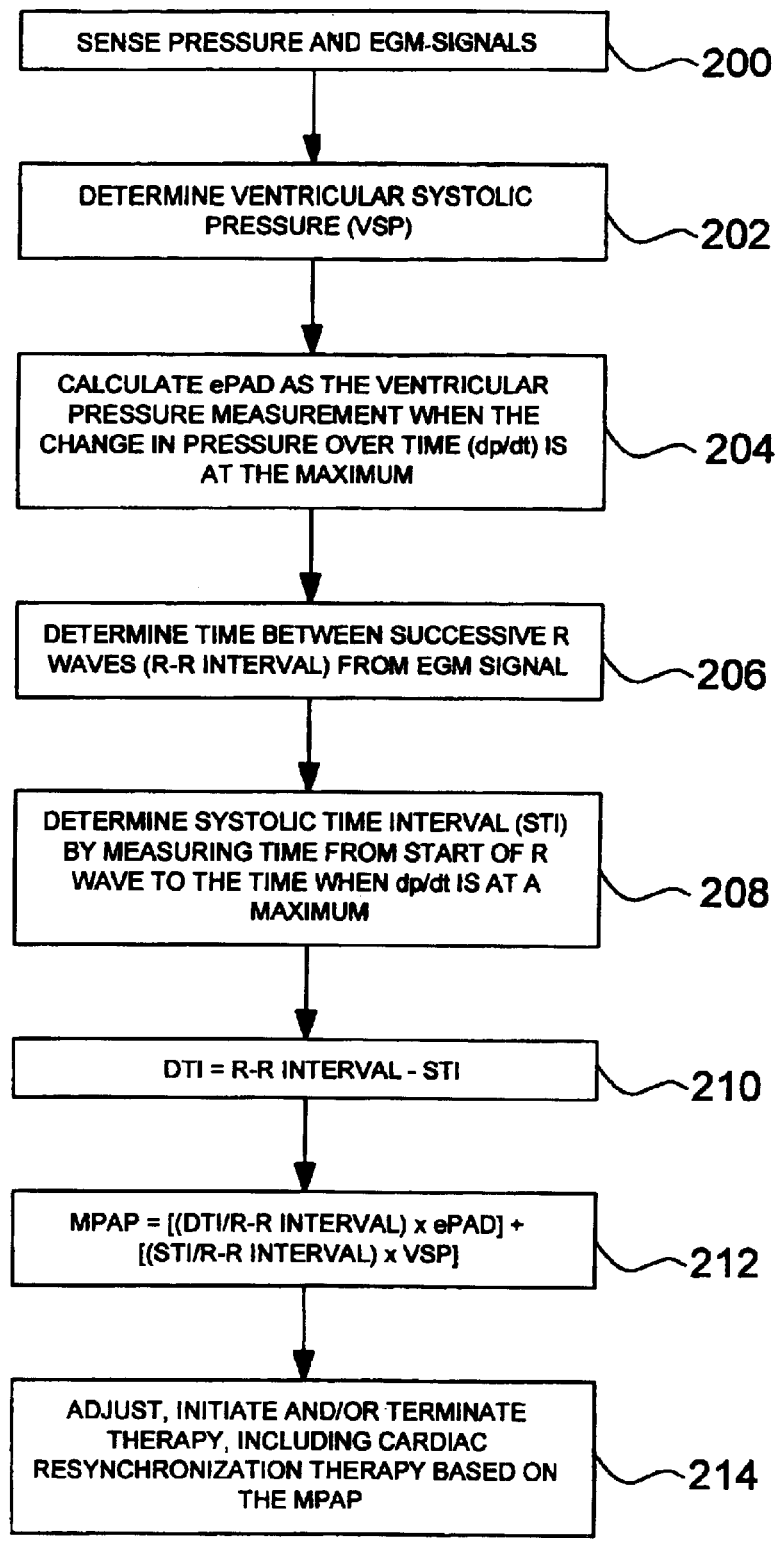
FIG. 4 is a flow diagram summarizing the method steps for determining the MPAP according to one embodiment of the invention.

FIG. 4 is a flow diagram summarizing the method steps for determining the MPAP according to one embodiment of the invention. It will be appreciated that the ordering of the steps is, in most cases, purely exemplary. Additionally, the steps may be performed either entirely by a processing circuit within an IMD, entirely by a processing circuit external to a living body, or by any combination thereof. Finally, the processing steps may be accomplished using any combination of analogue or digital hardware, software, firmware, microcode, or any other processing means.

According to the method of FIG. 4, ventricular pressure and EGM signals are sensed using any of the mechanisms discussed above (200). These signal values are generally digitized so that they may be processed using a digital processing circuit, but if an analog processing circuit is used, this need not be the case. Next, the VSP is determined as the maximum pressure that is measured at any time throughout the cardiac cycle (202). The estimated Pulmonary Artery Diastolic pressure (ePAD) is then determined as a measure of the ventricular pressure at the time the change in the pressure signal over time (dp/dt) is at a maximum (204). The time between successive R waves in the cardiac cycle (R—R interval) is measured using the EGM signal (206). The Systolic Time Interval (STI) may be estimated by measuring the time from the start of an R wave to the time when the change in pressure over time (dp/dt) is at a maximum (208). The Diastolic Time Interval (DTI) is determined by subtracting STI from the R—R Interval (210). Finally, Mean Pulmonary Arterial Pressure (MPAP) is determined (212) according to the following equation:

$$MPAP = [(DTI/R\text{—}R\ \text{Interval}) \times ePAD] + [(STI/R\text{—}R\ \text{Interval}) \times VSP].$$

After MPAP is derived, this value may be used to initiate, terminate, or adjust therapy. For example, if the MPAP is determined to be outside of an acceptable range, biologically-active agents may be delivered automatically by drug pump 150 (FIG. 2) under the control of controller 106 and microprocessor 100. For example, if the MPAP is too high, indicating pulmonary hypertension exists, arterial dilation may be accomplished by administering a drug such as Flolan. Alternatively, or additionally, electrical stimulation parameters may be adjusted.

In one embodiment, the estimated MPAP value may be used to adjust parameters associated with cardiac resynchronization therapy. As discussed above, this type of therapy involves pacing both the left and right ventricles to improve the efficiency of cardiac operation in heart failure patients. By adjusting pacing parameters such as A—V intervals or the V—V intervals between pacing pulses delivered in each of the ventricles, pulmonary pressure may be adjusted. Generally, in heart failure patients, this will involve adjusting parameters to lower arterial pressure, although arterial pressure may also be increased in a similar manner if necessary.

In yet another application of the invention, the MPAP value may be used to treat sleep apnea. Patients suffering from this type of sleep disorder experience a drop in pulmonary arterial pressure which may be detected using the MPAP. In response, pacing rate may be increased in patient's having an implantable pacemaker to counteract this drop in pressure.

It may be noted that in any of the above-described embodiments, a pressure sensor may be located in the left ventricle in addition to, or as an alternative to, a sensor in the right ventricle. This may be accomplished by guiding a lead or other similar structure carrying the sensor into the right ventricle, through the septal wall, and into the left ventricle. Alternatively, during an invasive procedure wherein the left ventricle is exposed, a lead may be directly inserted through the left ventricular wall into the left ventricular chamber. In either situation, this type of sensor placement is probably only desirable in patients that are already indicated for left ventricular lead placement for another purpose, since such lead placement increases the probability of stroke caused by blood clots. Additionally, such lead placement is generally accompanied by the administration of anticoagulation medication to prevent clotting.

Figure 5:
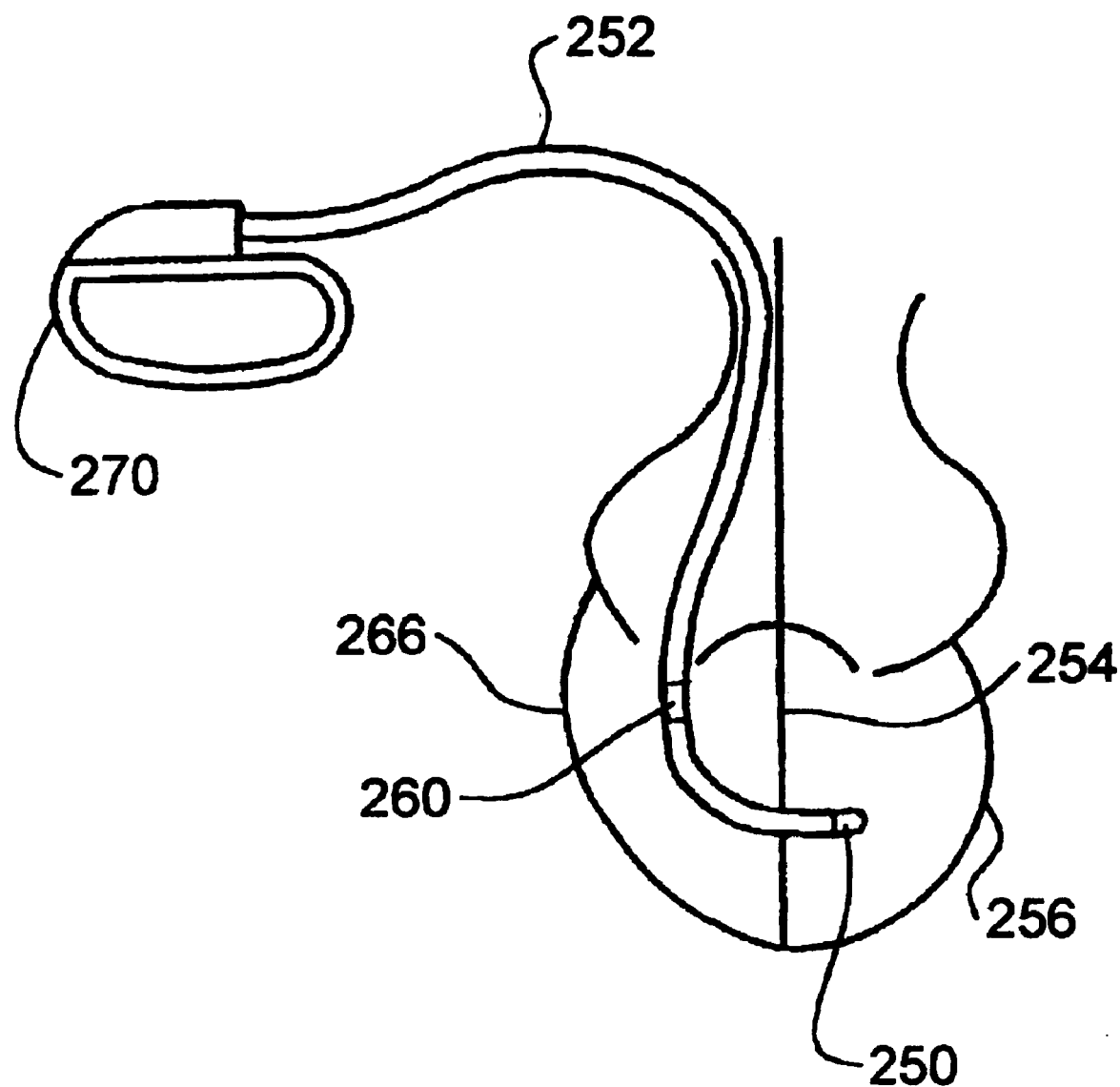
FIG. 5 is an exemplary embodiment wherein a pressure sensor is located in each of the left and right ventricles.

FIG. 5 is an exemplary embodiment illustrating a pressure sensor located in each of the left and right ventricles. A pressure sensor 250 at the distal end of the lead 252 is positioned through the septal wall 254 and located within the left ventricle 256. A second pressure sensor 260 is located proximal pressure sensor 250 on lead 252 within the right ventricle 266. The lead is coupled to IMD 270. Using this configuration, MPAP estimates may be derived using pressure measurements from both sides of the heart. If desired, only one of the pressure sensors need be activated at a given time using switching logic within the IMD. The two MPAP values derived using left and right ventricular pressures may be further processed, as by obtaining an average value, for example. In an alternative embodiment, the sensors shown in FIG. 5 may be carried on separate leads. In yet another embodiment, only pressure sensor 250 is provided to measure the left ventricular pressure.

Studies have been conducted to compare the MPAP as determined by the current invention to mean arterial pressure measurements obtained using a pressure sensor located in the patient's pulmonary artery. Data was collected for subjects undergoing various hemodynamic stressors. These studies conclude that the inventive system and method provides a MPAP measurement that closely approximates pressure values that would be measured using a pressure sensor located within the pulmonary artery.

Figure 6:
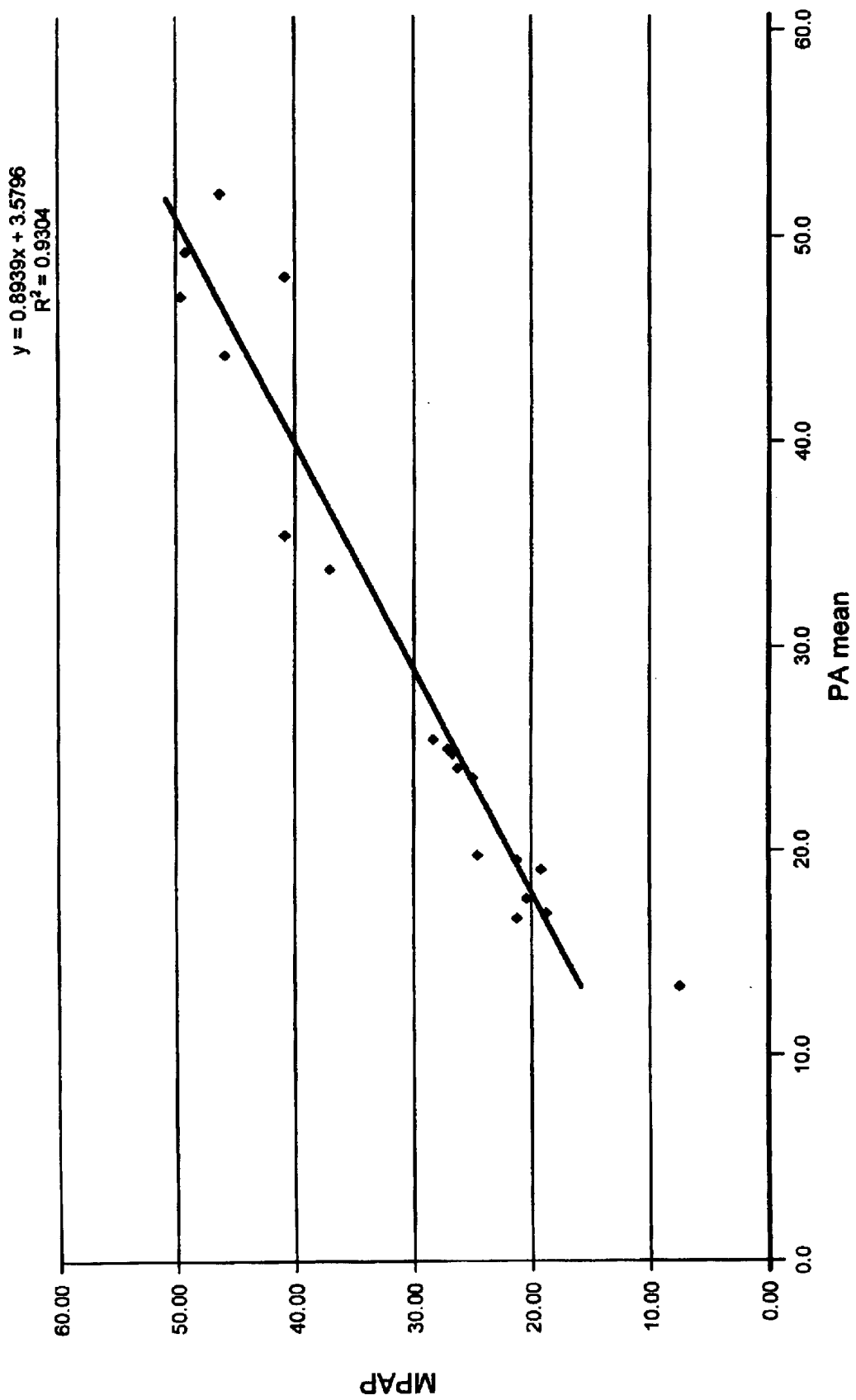
FIG. 6 is a graph comparing pressure measurements obtained using a pressure sensor located within an artery to estimated MPAP values obtained using the method of the current invention.

FIG. 6 is a graph illustrating the results of one study comparing MPAP estimates obtained using the current invention to mean arterial pressure measurements. The measured pulmonary artery pressure is processed using the integration method discussed above. The MPAP estimates are shown on the Y axis, whereas the measured pulmonary arterial pressure values are illustrated on the X axis labeled as "PA mean". It may be noted that a slope of "one" for the resulting line indicates a perfect correlation between the MPAP and the PA mean. The graph shows the close correlation between the estimated MPAP and the actual measured mean pulmonary arterial pressure PA.

Other scopes and aspects of the current invention will be appreciated by one skilled in the art from the above description of the inventive system and method, and the attached drawings.

What is claimed is:

1. A system for determining mean pulmonary arterial pressure of a patient, comprising:
   a first sensor adapted to be located in a ventricle of a heart to measure ventricular pressure;
   a first circuit to measure electrocardiogram (EGM) signals; and
   a processing circuit coupled to receive signals indicative of the ventricular pressure and the EGM signals, and to determine there from, mean pulmonary arterial pressure (MPAP).

2. The system of claim 1, wherein the first circuit includes at least one electrode adapted to be located within the cardiac vascular system of the patient.

3. The system of claim 1, wherein the first circuit includes at least two electrodes adapted to be placed on an external surface of the patient.

4. The system of claim 1, wherein the first circuit is located within an implantable device, and wherein the first circuit includes at least one electrode adapted to be positioned adjacent to a housing of the implantable device.

5. The system of claim 1, wherein the first sensor is adapted to be located within a first ventricle of the heart, wherein the system includes a second sensor adapted to be located within the other ventricle of the heart, and wherein the processing circuit includes means to estimate the MPAP from pressure measured by both the first and second sensors.

6. The system of claim 1, wherein the processing circuit is located within an implantable device.

7. The system of claim 1, wherein the processing circuit is adapted to be located in a device external to the patient, and wherein the system further includes a communication circuit to transfer indications of the measured pressure and the EGM signals to the processing circuit.

8. The system of claim 1, wherein the processing circuit includes first and second portions, wherein the first portion is located within an implantable device, wherein the second portion is located within a device adapted to be external to the patient, and wherein the system further includes a communication circuit to transfer data signals between the first and second portions.

9. The system of claim 1, and further including a therapy delivery circuit coupled to the processing circuit to provide therapy to the patient.

10. The system of claim 1, wherein the processing circuit includes means for controlling the therapy delivery circuit based on the estimated MPAP.

11. The system of claim 10, wherein the therapy delivery circuit includes a circuit to provide cardiac resynchronization therapy to the patient.

12. The system of claim 10, wherein the therapy delivery circuit includes a drug delivery device to deliver a biologically-active agent to the patient.

13. A method of determining mean pulmonary arterial pressure (MPAP), comprising:
   a.) sensing pressure within a ventricle of a heart;
   b.) sensing an electrocardiogram (EGM) signal of the heart; and
   c.) using the sensed pressure and the EGM signal to derive the MPAP.

14. The method of claim 13, wherein step c.) includes deriving a systolic time interval indicative of time spent by the heart in systole, and a diastolic time interval indicative of time spent in diastole.

15. The method of claim 14, wherein step c.) includes deriving the systolic time interval by measuring from a start of an R-wave of the EGM signal to a time when a change in sensed pressure over time is at a maximum.

16. The method of claim 15, wherein step c.) further includes utilizing the sensed pressure to determine a Ventricular Systolic Pressure (VSP), wherein the VSP is substantially a maximum pressure measured at any time during a cardiac cycle of the heart.

17. The method of claim 16, wherein step c.) further includes utilizing the sensed pressure to determine an estimated Pulmonary Arterial Diastolic pressure (ePAD), wherein the ePAD is a pressure measured substantially at a time in the cardiac cycle wherein the change in the sensed pressure over time is at a maximum.

18. The method of claim 17, and further including:
   c.) multiplying the diastolic time interval by the ePAD;
   d.) multiplying the systolic time interval by the VSP; and
   e.) adding the values obtained in steps c.) and d.) to obtain the MPAP.

19. The method of claim 13, and further comprising delivering therapy based on the MPAP.

20. The method of claim 19, and further comprising delivering a biologically-active agent to the patient based on the MPAP.

21. The method of claim 19, and further comprising delivering cardiac resynchronization therapy to the patient based on the MPAP.

22. The method of claim 21, and further comprising modifying timing parameters of the cardiac resynchronization therapy based on the MPAP.

23. A system for deriving mean pulmonary arterial pressure (MPAP) of a patient, comprising: pressure sensing means adapted to be located in a ventricle of a heart for measuring pressure in the ventricle; EGM sensing means for sensing an electrocardiogram (EGM) signal; and processing means for deriving the (MPAP) based on the measured ventricular pressure and the EGM signal.

* * * * *